United States Patent [19]

Beregi et al.

[11] 4,032,658
[45] June 28, 1977

[54] ALKANOLAMINE DERIVATIVES

[75] Inventors: Laszlo Beregi, Boulogne; Pierre Hugon, Rueil-Malmaison; Jacques Duhault, Chatou; Michelle Boulanger, Marly le Roi, all of France

[73] Assignee: Science-Union et Cie, Suresnes, France

[22] Filed: Apr. 23, 1975

[21] Appl. No.: 570,876

[30] Foreign Application Priority Data

Apr. 30, 1974 United Kingdom ............ 18838/74

[52] U.S. Cl. .................. 424/309; 260/239 BA; 260/243 B; 260/247.2 B; 260/293.78; 260/326.27; 260/326.43; 260/472; 424/244; 424/246; 424/248; 424/55; 424/267; 424/274

[51] Int. Cl.² ...................................... C07C 101/04

[58] Field of Search .................. 260/472; 424/309

[56] References Cited

UNITED STATES PATENTS 3,759,979  9/1973  Beregi et al. ............... 424/309 X
3,868,416  2/1975  Albright et al. ............. 260/472 X Primary Examiner—Richard L. Raymond
Attorney, Agent, or Firm—Gordon W. Hueschen

[57] ABSTRACT

Alkanolamine derivatives and their optical isomers of the formula:

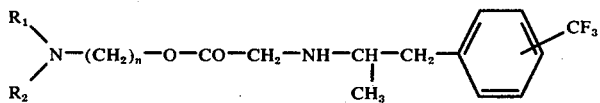

wherein:
$n$ is 2 or 3, and
$R_1$ and $R_2$ are lower alkyl or taken together with the nitrogen to which they are bonded, they form pyrrolidinyl, piperidino, dimethyl piperidino, morpholino, 1-thiomorpholino, azabicyclo [3, 3, 0] octyl or azabicyclo [3, 2, 2] nonyl.

These compounds are used as medicines especially in the treatment of obesity, atheroma or metabolic diseases requiring weight reduction and regulation.

6 Claims, No Drawings

ALKANOLAMINE DERIVATIVES

The present invention provides alkanolamine derivatives of the general formula I :

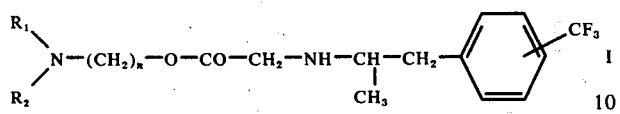

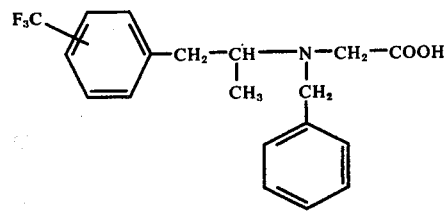

wherein:
n is selected from 2 and 3,
$R_1$ and $R_2$ which are the same or different, are each selected from the group consisting of alkyl radicals, in linear and branched chain, having from 1 to 4 carbon atoms inclusive, and $R_1$ and $R_2$ taken together with the nitrogen atom to which they are bonded, represent a heterocyclic radical selected from the group consisting of pyrrolidinyl, piperidino, dimethylpiperidino, morpholino, 1 - thiomorpholino, azabicyclo [3, 3, 0] octyl and azabicyclo [3, 2, 2 ] nonyl radicals.

The trifluoromethyl radical may be on ortho, meta or para position with regards to the lateral chain, nevertheless, the meta position is the preferred one.

Due to their pharmacological properties, the preferred compounds are the compounds of the general formula I wherein n has the meaning given above and $R_1$ and $R_2$ each represents an alkyl radical having from 1 to 4 carbon atoms in a linear or branched chain.

The present invention also provides acid addition salts especially physiologically tolerable acid addition salts of compounds of the general formula I with mineral or organic acids. As acids which may be used to form such addition salts, there may be mentioned, for example, in the mineral series : hydrochloric, hydrobromic, sulfuric and phosphoric acids, and in the organic series : acetic, propionic, maleic, fumaric, tartaric, citric, oxalic, benzoic, methanesulfonic and isethionic acids.

All the compounds of general formula I possess an assymetric carbon atom and exist in form of optically active isomers which are also included in the present invention. These optical isomers may be prepared from the d or l 1-(trifluoromethylphenyl)-2 benzylamino propane.

A large number of fenfluramine derivatives are known in the art to have noteworthy anorectic properties always accompanied by marked sedative effect.

It has now been surprisingly found that the ethanolamine and propanolamine esters of the present invention have practically no demonstrable sedative effect at anorectic doses.

Moreover, for the first time in the fenfluramine related compounds, the d isomers present real advantages over the racemic counterparts.

The compounds of the general formula I are new and they are prepared according to the following processes, which are included in the present invention.

The present invention provides a process for preparing compounds of the general formula I which comprises : - reacting a dl, d or l N-(1-trifluoromethylphenyl - 2 -propyl) - N - benzyl glycine of the general formula II :

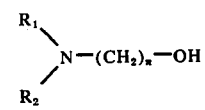

with an amino alkanol of the general formula III :

wherein $R_1$, $R_2$ and n have the meanings previously given, then, hydrogenating the so obtained dl, d or l glycinate of the general formula IV :

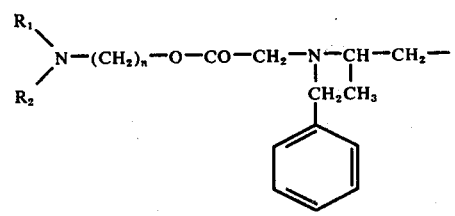

wherein $R_1$, $R_2$ and n have the meanings given above, in order to separate the benzyl group.

Such an hydrogenation of the compound IV is advantageously carried out in an anhydrous solvent such for example as anhydrous dimethylformamide, under a hydrogen pressure of 6kg/cm², in the presence of palladised charcoal containing 5% by weight of palladium.

The reaction of compounds II and III is easily performed in an anhydrous solvent, such as for example as, anhydrous tetrahydrofuran, in the presence of an anhydrous tertiary amine, such for example as treithylamine, and ethyl chloroformate.

The starting dl, d or l compounds of the general formula II are prepared starting from the corresponding dl, d or l lower alkyl glycinates, such for example, dl, d or l ethyl N-(1-trifluoromethylphenyl - 2 propyl) - N - benzyl glycinate, themselves prepared starting from the corresponding dl, d or l 1 -trifluoromethylphenyl - 2 benzylamino propanes.

The d and l 1 -trifluoromethylphenyl - 2 - benzylamino propanes are prepared starting from the corresponding racemic compounds, the resolution being made according to classical methods, by the means, for example, of d (+) camphosulfonic acid, and d (−) dibenzoyl tartaric acid.

The present invention also provides a process for preparing compounds of the general formula I which comprises reacting a dl, d or l ethyl N - (1 - trifluoromethylphenyl - 2 - propyl) glycinate of the general formula V:

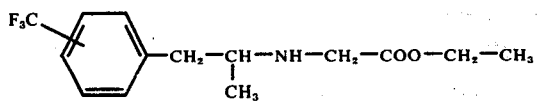

with an aminoalkanol of the general formula III given above.

Such a reaction is advantageously carried out by refluxing the reactants in the presence of sodium methylate.

The racemic compounds and their isomers of the general formula I and physiologically tolerable acid addition salts thereof possess valuable pharmacological and therapeutic activities, particularly appetite inhibiting and lipids and carbohydrates metabolism regulating properties. They so can be used as medicines especially in the treatment of obesity, atheroma or other metabolic diseases needing weight reduction and regulation.

Their toxicity is low and their $LD_{50}$ determined in mice varies from 600 to 1 600 mg/kg by the oral route.

The anorexigenic activity was studied in rats. The food intake was reduced by 50%, 2 hours after administering the products at the dose of 1,9 to 15 mg/kg P.O.

The present invention also provides pharmaceutical preparations containing as active ingredient a dl, d or l compound of the general formula I, or a physiologically tolerable salt thereof, in admixture or conjunction with a pharmaceutically suitable carrier, such for example as distilled water, glucose, lactose, starch, talc, magnesium stearate, ethyl cellulose or cocoa-butter.

The so-obtained pharmaceutical compositions are advantageously in unit dosage form and may contain from 5 to 100 mg of the active ingredient. They may be in the form of tablets, dragees, capsules, suppositories or injectable or drinkable solutions and administered by oral, rectal or parenteral route at a dose of 5 to 100mg 1 to 5 times a day.

The following Examples illustrate the invention, the parts being by weight and the melting points being determined on a Kofler hot plate.

EXAMPLE 1 d 1-(3 - trifluoromethylphenyl) - 2 -benzylamino propane

To a suspension of 725 parts of d (+) camphosulphonic acid in 3 000 parts of ethyl acetate, there were added, in 5 minutes, 850 parts of racemic 1 - (3 - trifluoromethylphenyl) - 2-benzylamino propane. The mixture was refluxed for 10 minutes. After being allowed to cool to 40° C without stirring, the precipitate was filtered off, washed twice with 200 parts of ethylacetate, and then air-dried, 588 parts of d (+) camphosulphonate were obtained, melting at 133°–137° C.

After recrystallization from ethyl acetate, 475 parts of pure salt was obtained (M.P. 143°–144° C) and placed in suspension in 2 000 parts of water. After alkalinisation with 500 parts of caustic soda lye in presence of 2 000 parts of ether, the organic layer was separated. The remaining aqueous layer was then extracted with 1 000 parts of ether. The organic layers were then put together, dried over anhydrous magnesium sulphate and concentrated in vacuo. Upon distillation under reduced pressure, there were obtained 241 parts of d 1 - (3 - trifluoromethylphenyl) - 2 -benzylamino propane boiling at 120°–122° C at 0.3 millimeter pressure, $[\alpha]_D^{24}$ : +27.25° (pure base, tube 10 cm).

EXAMPLE 2 l 1 - (3- trifluoromethylphenyl) - 2-benzylamino propane

The mother liquor of the example 1 was evaporated under vacuo and the residue was treated with 3 000 parts of water and 1 000 parts of caustic soda lye, then extracted twice with 1 500 parts of ether. After drying, the solvent was evaporated and the residue was distilled. 469.5 parts of base was obtained, B.P./0.3 mm Hg : 122°–126° C,$[\alpha]_D^{24}$ : 14.7° (pure base, tube 10 cm).

438 parts of this base were poured for 8 minutes in a solution of 617 parts of d (−) dibenzoyl tartaric acid in 2 500 of anhydrous ethanol.

The precipitate thus obtained was filtrated, washed twice with 100 parts of ethanol and air-dried. 532 parts of d (−) dibenzoyl tartrate were obtained, melting at 191°–192° C.

After 3 recrystallizations from ethanol, 192 parts of pure salt were finally obtained (M.P. 193°–194° C) and placed in a suspension with 1 000 parts of water, 500 parts of caustic soda lye and 1 000 parts of ether. The organic layer was separated, the remaining aqueous layer was then extracted with 500 parts of ether.

The organic layers were then put together, dried and concentrated in vacuo. Upon distillation under reduced pressure, there were obtained 93.5 parts of l 1 - (3-trifluoromethylphenyl) - 2 - benzylamino propane, $[\alpha]_D^{26}$ : − 26.7° (pure base, tube 10 cm).

EXAMPLE 3 dl Ethyl N - [1 - (3 - trifluoromethylphenyl) - 2 - propyl] - N - benzyl glycinate A mixture of 92 parts of 1 - (3 - trifluoromethylphenyl) - 2 -benzylamino propane, 57.6 parts of ethyl bromoacetate, 47.6 parts of potassium carbonate and 300 parts of ethanol was refluxed for 6 hours. After being allowed to cool at room temperature, the salt was filtered off. The distillation of the residual liquid yielded 85 parts of dl Ethyl N - [ 1 -(3 - trifluoromethylphenyl) - 2-propyl] - N -benzyl glycinate, B.P./0.2 mm Hg : 160°–162° C.

EXAMPLES 4–5

The following compounds were prepared according to the method described in Example 3, from d 1 - (3-trifluoromethylphenyl)-2 - benzylamino propane, and l 1 - (3 -trifluoromethylphenyl)-2 - benzylamino propane.

4. d Ethyl N - [ 1 - (3 -trifluoromethylphenyl) - 2-propyl] - N -benzyl glycinate, B.P./0.15 − 0.2 mm Hg : 149°–150° C.

5. l Ethyl N -[ 1 -(3 - trifluoromethylphenyl) - 2 -propyl] - N - benzyl glycinate, B.P./0.2 mm Hg : 163°–165° C.

EXAMPLE 6 dl N - [ 1 - (3 - trifluoromethylphenyl) - 2 - propyl] - N - benzyl glycine 356 parts of dl Ethyl N - [ 1 - (3 - triflüromethylphenyl) - 2 - propyl]- N - benzyl glycinate prepared according to the Example 3 were added to 990 parts of 2.5 N Na OH and 1 000 parts of ethanol. The mixture was refluxed for 1 hour The solvent was evaporated in vacuo. The residue was treated with 1 500 parts of water and acidified with 930 parts of 2.7 N HCl. The resulting oil was extracted twice with 1 000 parts of chloroform. After drying the solvent was evaporated and the residue was treated with 100 parts of ethyl acetate and 1 500 parts of petroleum ether. The precipitate was filtered off and dried in vacuo. There were obtained 329 parts of dl N - [1 - (3 - trifluoromethylphenyl) - 2 - propyl]- N - benzyl glycine, Its hydrochloride, recrystallized from isopropanol, melts at 174°–176° C.

EXAMPLES 7–8

The two optical isomers were prepared according to the method described in Example 6.

7. d N -[1 - (3 -trifluoromethylphenyl) - 2-propyl]- N - benzyl glycine, M.P. 92°–94° C (ethyl acetate/petroleum ether), $[\alpha]_D^{24}$ + 25.5° (C.20, acetic acid)-, $[\alpha]_D^{24}$ : + 23.7° (C.20, dimethylformamide).

8. 1 N -[1 - (3 - trifluoromethylphenyl) - 2 -propyl]- N - benzyl glycine, M.P. 92°–94° C (ethyl acetate/petroleum ether).

EXAMPLE 9 d β-dimethylaminoethyl N - [1 - (3 - trifluoromethylpehnyl) - 2 - propyl] - N - benzyl glycinate To a solution of 28 parts of d N -[1 - (3 - trifluoromethylphenyl) - 2 - propyl] - N - benzyl glycine in 150 parts of anhydrous tetrahydrofuran, there were added 8 parts of anhydrous triethylamine.

The solution thus obtained was poured for 1 hour to a solution of 8.7 parts of ethyl chloroformate in 40 parts of anhydrous tetrahydrofuran maintained at 0°–5° C. 7.1 parts of β-dimethylaminoethanol were then added, while stirring at room temperature. The reaction mixture was then refluxed for 3 hours and the resulting triethylamine hydrochloride filtered off. The liquid residue was concentrated in vacuo and distilled. There was thus obtained 26.5 parts of d β-dimethylaminoethyl N - [1-(3 - trifluoromethylphenyl) - 2-propyl] - N - benzyl glycinate, B.P./0.6 mm Hg : 180°–186° C.

EXAMPLES 10–26

The following compounds were prepared according to the method described in Example 9.

10. 1 β - dimethylaminoethyl N - [1 - (3 - trifluoromethylphenyl) - 2 -propyl] - N -benzyl glycinate, B.P./0.3–0.4 mm Hg : 176°–181° C.

11. dl β-dimethylaminoethyl N -[1 - (3 - trifluoromethylphenyl) - 2 -propyl] - N - benzyl glycinate, B.P./0.1 mm Hg : 168°–171° C.

12. dl γ-dimethylaminopropyl N -[1 (3 - trifluoromethylphenyl) - 2 - propyl] - N - benzyl glycinate, B.P./0.35 mm Hg : 187°–195° C.

13. d γ-dimethylaminopropyl N -[1 - (3 -trifluoromethylphenyl) - 2 -propyl] - N - benzyl glycinate.

14. 1 γ-dimethylaminopropyl N -[1 - (3 -trifluoromethylphenyl) - 2 - propyl] - N - benzyl glycinate.

15. dl β-diethylaminoethyl N -[1 - (3 -trifluoromethylphenyl) - 2 -propyl] - N - benzyl glycinate, B.P./0.4 mm Hg : 185°–188° C.

16. d β-diethylaminoethyl N-[1 - (3 - trifluoromethylphenyl) - 2 -propyl] - N - benzyl glycinate, B.P./0.5 mm Hg : 189°–190° C.

17. 1 β-diethylaminoethyl N -[1 - (3 - trifluoromethylphenyl) - 2 -propyl]- N -benzyl glycinate, B.P./0.1 mm Hg : 180°–185° C.

18. dl β-piperidinoethyl N -[1 - (3 - trifluoromethylphenyl) - 2 -propyl]- N - benzyl glycinate, B.P./0.2 mm Hg : 186°–192° C.

19. d β-piperidinoethyl N - [1 - (3 -trifluoromethylphenyl) - 2 - propyl] - N - benzyl glycinate.

20. 1 β-piperidinoethyl N - [1 - (3 - trifluoromethylphenyl) - 2 propyl]- N - benzyl glycinate.

21. dl β- diisopropylaminoethyl N - [1 - (3 -trifluoromethylphenyl) - 2 - propyl]- N - benzyl glycinate, B.P./0.4 – 0.6 mm Hg : 184°–205° C.

22. d β- diisopropylaminoethyl N - [1 - (3 - trifluoromethylphenyl) - 2 - propyl] - N - benzyl glycinate.

23. 1 β-diisopropoylaminoethyl N -[1 - (3 -trifluoromethylphenyl) - 2 - propyl]- N - benzyl glycinate.

24. dl β -[3 - azabicyclo (3.3.0) oct - 3 - yl]-ethyl N -( 1 - (3 -trifluoromethylphenyl) - 2 -propyl] - N - benzyl glycinate, B.P./0.15 mm Hg : 200°–210° C.

25. d β-[3 - azabicyclo (3.3.0) oct-3-yl]-ethyl N -[1 - (3 -trifluoromethylphenyl) - 2 -propyl] - N - benzyl glycinate.

26. 1 β-[3 - azabicyclo (3.3.0) oct-3-yl]-ethyl N-[1 -(3 trifluoromethylphenyl) - 2 -propyl] - N - benzyl glycinate.

EXAMPLE 27 dl β-dimethylaminoethyl N - [1 - (3 trifluoromethylphenyl) - 2 - propyl] glycinate

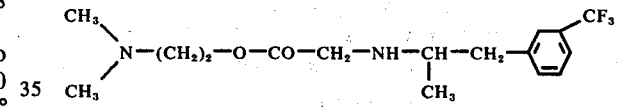

26.5 parts of dl β-dimethylaminoethyl N - [1 - (3 -trifluoromethylphenyl) - 2 - propyl]-N - benzyl glycinate in a solution of 120 parts of anhydrous dimethylformamide were hydrogenated over 4 parts of Pd/C 5% at a pressure of 6Kg/cm² in view of the separation of the benzyl group. The solvent was evaporated under reduced pressure and the residue distilled ; there was obtained dl β- dimethylaminoethyl N - [1 - (3 -trifluoromethylphenyl) - 2 -propyl]glycinate, B.P./0.5 mm Hg : 136°–138° C, M.P. of its dihydrochloride hemihydrate : 212° C (isopropanol).

EXAMPLES 28–44

The following compounds were prepared according to the method described in Example 27 :

28. d β- dimethylaminoethyl N - [1 - (3 - trifluoromethylphenyl) - 2 - propyl] glycinate, B.P./0.4 mm Hg : 131°–133° C,$[\alpha]_D^{27}$ : + 7.90° (pure base, tube 10cm) ; for its dihydrochloride : M.P. 215°–216° C (isopropanol), $[\alpha]_D^{25}$ : + 6° (C.10, CH₃ COOH)

29. 1 β-dimethylaminoethyl N - [1 - (3 - trifluoromethylphenyl) - 2-propyl] glycinate, B.P./0.25 mm Hg : 128°–130° C,$[\alpha]_D^{27}$ =− 7.3° (pure base, tube 10 cm); for its dihydrochloride M.P. 215°–216° C, [α]HD D²⁶ = − 6.5° (c.10, CH₃ COOH).

30. dl β-diethylaminoethyl N -[1 - (3 -trifluoromethylphenyl) - 2 - propyl] glycinate, B.P./0.1 mm Hg : 142°–144° C, M.P. of its dihydrochloride : 224°–225° C (isopropanol).

31. d β-diethylaminoethyl N - [1 - (3 -trifluoromethylphenyl) - 2 -propyl] glycinate, B.P./0.3 mm Hg : 142°–143° C,$[\alpha]_D^{24}$ : + 7.9°; (pure base, tube 10 cm).

32. l β- diethylaminoethyl N -[1 - (3 -trifluoromethylphenyl) - 1 -propyl] glycinate, B.P./0.1 mm Hg : 142°–143° C,[α]$_D^{23}$ = – 7.6° (pure base, tube 10 cm).

33. dlβ-piperidinoethyl N - [ 1 - (3 -trifluoromethylphenyl) - 2 - propyl] glycinate, B.P./0.15 mm Hg : 154°–156° C ; M.P. of its dihydrochloride hemihydrate : 152°–154° C, (acetone).

34. d β - piperidinoethyl N - [ 1 - (3 - trifluoromethylphenyl) - 2 - propyl] glycinate.

35. l β-piperidinoethyl N -[ 1 - (3 -trifluoromethylphenyl) - 2 - propyl] glycinate, 36. dl β-diisopropylaminoethyl N - [ 1 -(3 - trifluoromethylphenyl) - 2 - propyl] glycinate, M.P. 194°–197° C (sublimation).

37. d β-diisopropylaminoethyl N - [ 1 - (3 -trifluoromethylphenyl) - 2 - propyl] glycinate.

38. l β- diisopropylaminoethyl N -[ 1 - (3 -trifluoromethylphenyl) - 2 - propyl] glycinate.

39. dl β-[(3-azabicyclo (3.3.0) oct-3-yl] ethyl N -[ 1 - (3 -trifluoromethylphenyl) - 2 - propyl] glycinate, B.P./0.3 mm Hg : 175°–177° C.

40. d β- [(3 - azabicyclo (3.3.0) oct-3-yl] ethyl N -[ 1 - (3 - trifluoromethylphenyl) - 2 -propyl] glycinate.

41. l β-[(3 -azabicyclo (3.3.0) oct-3-yl] ethyl N -[ 1 - (3 -trifluoromethylphenyl) - 2 -] glycinate.

42. dl γ-dimethylaminopropyl N -[ 1 - (3 -trifluoromethylphenyl) - 2 -propyl] glycinate, M.P. 206°–208° C (sublimation).

43. d β- dimethylaminopropyl N -[ 1 - (3 -trifluoromethylphenyl) - 2 -propyl]glycinate.

44. l γ-dimethylaminopropyl N - [ 1 - (3 -trifluoromethylphenyl) - 2 - propyl] glycinate.

EXAMPLE 45 dl β- dimethylaminoethyl N -[ 1 - (3 -trifluoromethylphenyl) - 2 - propyl] glycinate In a 3 000 ml three-necked flask equipped with a stirrer, a thermometer, a column of 20 cm height, a downward directed condenser and a receiver, there were mixed 1 200 parts of dl ethyl N -[ 1 - (3 -trifluoromethylphenyl) - 2 - propyl] glycinate, 740 parts of β-dimethylaminoethanol and 8 parts of sodium methoxide.

The reaction mixture was refluxed and the so-formed ethanol was distilled off. The heating was maintained until the temperature of the mass reach 160° C and the temperature of the fumes reach 124° C; which requires about 6 hours. Then the distillation was carried on under high vacuum. There were obtained 1 170 parts of dl β-dimethylamino ethyl N - [ 1 - (3 -trifluoromethylphenyl) - 2 -propyl] glycinate, B.P./0.5–0.8 mm Hg : 135°–150° C.

To a solution of 332 parts of this glycinate in 2 000 ml of acetone, there were quickly added 266 parts of hydrochloric acid (d : 1.19), then 4,000 ml of acetone. After cooling, the precipitate was suctioned off, washed with 2 000 ml of acetone and air-dried.

There were obtained 294 parts of dl β-dimethylaminoethyl N - [ 1 - (3 -trifluoromethylphenyl) - 2 - propyl] glycinate, dihydrochloride hemihydrate, melting at 216°–217° C.

Each compound of the examples 28 to 44 was also prepared according to the method described in Example 45, starting from dl, d or l ethyl N-[ 1 - (3 - trifluoromethylphenyl) - 2 -propyl] glycinate, and the suitable aminoalkanol.

We claim:

1. A compound selected from the group consisting of:

A. alkanolamine derivatives and their optical isomers of formula I:

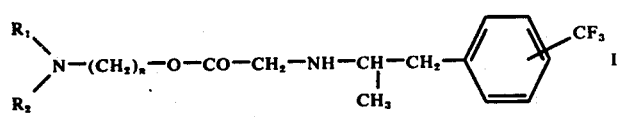

wherein:

n is 2 or 3 and $R_1$ and $R_2$ are each lower-alkyl having 1 to 4 carbon atoms inclusive, and B. physiologically tolerable acid addition salts thereof.

2. A compound of claim 1 which is dl β - dimethylaminoethyl N - [ 1 - (3 -trifluoromethylphenyl) - 2 - propyl] glycinate, and its optical isomers.

3. A compund of claim 1, which is dlβ-diethylaminoethyl N - [ 1 - (3 -trifluoromethylphenyl) - 2 - propyl] glycinate, and its optical isomers.

4. A compound of claim 1 which is dl γ-dimethylaminopropyl N - [ 1 - (3 - trifluoromethylphenyl) - 2 - propyl] glycinate and its optical isomers.

5. A pharmaceutical composition containing as active principle at least one compound of claim 1 in an amount of 5 to 100 mg together with a suitable pharmaceutical carrier.

6. A method of treating a living animal body afflicted with obesity, atheroma, or other metabolic disease requring weight reduction or regulation, comprising the step of administering to said living animal body an amount of a compound of claim 1 which is effective for such purpose.

* * * * *

UNITED STATES PATENT OFFICE
CERTIFICATE OF CORRECTION

Patent No. 4,032,658　　　　　　　Dated June 28, 1977

Inventor(s) Laszlo Beregi et al

It is certified that error appears in the above-identified patent and that said Letters Patent are hereby corrected as shown below:

Col. 5, line 10; "cine," should read --cine, M.P. 80°C.
Col. 6, line 60; " $[\alpha]$ HD $D^{26}$" should read -- $[\alpha]_D^{26}$ --.

Col. 7, line 2; "phenyl)-1-propyl" should read --phenyl)-2-propyl--
Col. 7, line 26; "(3-trifluoromethylphenyl)-2-]" should read --(3-trifluoromethylphenyl-2-propyl]--
Col. 8, line 37; "compund" should read --compound--
Col. 8, line 49; "requring" should read --requiring--

Signed and Sealed this

Second Day of May 1978

[SEAL]

Attest:

RUTH C. MASON
Attesting Officer

LUTRELLE F. PARKER
Acting Commissioner of Patents and Trademarks